(12) United States Patent
Durán Toro et al.

(10) Patent No.: US 8,536,536 B2
(45) Date of Patent: Sep. 17, 2013

(54) METHOD AND SYSTEM FOR MEASURING THE CONCENTRATION OF DIFFERENT COMPOUNDS PRESENT IN PARTICULATE MATERIAL

(75) Inventors: Mario Manuel Durán Toro, Santiago (CL); Ronald Romeo Guzman Venegas, Santiago (CL)

(73) Assignee: Ingenieros Matematicos Consultores Asociados, S.A., Santiago (CL)

( * ) Notice: Subject to any disclaimer, the term of this patent is extended or adjusted under 35 U.S.C. 154(b) by 257 days.

(21) Appl. No.: 13/127,660

(22) PCT Filed: Nov. 3, 2009

(86) PCT No.: PCT/IB2009/054885
§ 371 (c)(1),
(2), (4) Date: Jul. 13, 2011

(87) PCT Pub. No.: WO2010/052645
PCT Pub. Date: May 14, 2010

(65) Prior Publication Data
US 2011/0260073 A1    Oct. 27, 2011

Related U.S. Application Data

(60) Provisional application No. 61/111,186, filed on Nov. 4, 2008.

(51) Int. Cl.
*G01J 1/42*     (2006.01)
*G01N 21/01*    (2006.01)
*G01N 33/24*    (2006.01)
*G01N 15/02*    (2006.01)

(52) U.S. Cl.
USPC .............................. 250/373; 250/435; 436/25

(58) Field of Classification Search
USPC ................... 250/373, 435; 436/25; 356/335
See application file for complete search history.

(56) References Cited

U.S. PATENT DOCUMENTS 5,351,686 A    10/1994    Steuer et al.
5,741,707 A    4/1998    Herron et al.
(Continued)

FOREIGN PATENT DOCUMENTS

WO    WO 95/09962       4/1995
WO    WO 2006/138632   12/2006
WO    WO 2008/017107    2/2008

OTHER PUBLICATIONS

International Search Report for International Application No. PCT/IB2009/054885 mailed Feb. 16, 2010 (Form PCT/ISA/210).
Gordon et al. "Improving grade control through Borehole Geophysics: Case Study from Iron Ore Company of Canada." http://www.quantecgeoscience.com/News/ArticlesPublications.php (2000).

(Continued)

*Primary Examiner* — David Porta
*Assistant Examiner* — Kenneth J Malkowski
(74) *Attorney, Agent, or Firm* — Merchant & Gould P.C.

(57) ABSTRACT

The present invention comprises a method and a system of collection and analysis for in situ determination of concentrations of minerals in granular material originating from a shaft under excavation, in a continuous, non-intrusive manner in real time. According to the present invention granular material collected passes to a granular material collector, subsequently entering a reading module which determines the concentration of different materials by spectroscopic methods. The granular material collected comes from drilling dust which rises along a boring tool of an excavating bit. The concentration data of different minerals in the granular material being analysed at a given moment may be processed and transmitted to establish and/or correct logistic and operational procedures such as, for example, in an excavation or in an overall process wherein it is set.

16 Claims, 2 Drawing Sheets

(56) References Cited

U.S. PATENT DOCUMENTS 5,780,848 A     7/1998    Thompson et al.
7,667,838 B2 *   2/2010    Ackerman et al. ............ 356/335

OTHER PUBLICATIONS

Turler et al. "Improved Process Control Through Real-Time Measurement of Mineral Content." http://www.osti.gov/bridge (2001).

* cited by examiner

METHOD AND SYSTEM FOR MEASURING THE CONCENTRATION OF DIFFERENT COMPOUNDS PRESENT IN PARTICULATE MATERIAL

This application is a National Stage Application of PCT/IB2009/054885, filed 3 Nov. 2009, which claims benefit of U.S. Ser. No. 61/111,186, filed 4 Nov. 2008 and which applications are incorporated herein by reference. To the extent appropriate, a claim of priority is made to each of the above disclosed applications.

BACKGROUND

The present invention is related, among others, to the geological, mining, particulate production, construction, and quality control industry, and it consists of a method and system for measuring the concentration of different compounds in a particulate material. Its applications include the measurement of the concentration of valuable minerals found in the dust of excavation pits.

For the determination of the concentration of valuable minerals, the commonly used methods in the prior art consider the analysis of samples of dust generated by the drilling of pits that is carried out in an area where the feasibility of exploitation is to be determined. The analysis of dust or debris produced in the drilling of pits is done, after performing the sample selection, either on-site or in a laboratory. The known methods of the prior art for analyzing the concentration of valuable materials use different properties of materials of interest to determine their presence and to what extent they are present.

Generally, the dust generated during the excavation of a pit are removed either manually or mechanically, often in an intrusive manner, and taken to laboratories where they are analyzed using chemical or other similar tests to determine the grade.

From prior art the international patent application WO2008/017.107 is known, entitled 'Characterization of geological materials by induced thermal response', which proposes a method and a device for identifying compounds in rocks. The method consists in radiating electromagnetically the rock, preferably with microwaves, to induce a response that manifests itself in temperature changes in the rock, which is then measured using an infrared camera. The infrared image data are analyzed and interpreted in terms of a database. As possible application is mentioned the introduction of this device in pits dug to identify the composition of its walls. However, the application of this method would first suppose the digging of a pit and the measurement would be done at different depths that should be chosen previously.

Another related prior art document is the international patent application WO95/09.962, entitled 'System for the continuous sampling of soils', which discloses a system for capturing samples of the material excavated from a pit. Disclosed is a container that can be lowered into the pit hanging from cable and that captures the samples once inside. After the capture, the samples can be raised to be analyzed. As usual in the prior art, the samples have to be handled and transported to a laboratory for analysis and to determine the concentration degree of the ore.

Also known is the publication entitled 'Enhancing the grade control through borehole geophysics: A case study from the Iron Ore Company of Canada', Robert L. Gordon, Tim Leriche, Susanne MacMahon; published during the year 2000, available on the Internet, URL: 'http://www.quantec-geoscience.com/News/ArticlesPublications.php'). This document describes the type of information that can be obtained from the soil to be exploited, in the depth and extension of the terrain, using a probe that descends through the already excavated pits. This probe is equipped with several sensors that determine the magnetic susceptibility, the density and the electrical conductivity among other properties. We mention the relation between the presence of valuable minerals and the measured variables, obtained by comparison with measurements made using traditional methods. The system described in this document includes first making an excavation to obtain a pit and then inserting a probe through this pit, so time, energy, and resources are wasted on the excavation of pits that could be detected as sterile during an early stage.

It is known from prior art the patent WO2006/138632 (A2), entitled 'Elementary on-line spectroscopic analysis of particles driven by a gas flow'. This document proposes a device through which a gas stream circulates that contains the particles to be analyzed. Inside this device a laser beam turns a small portion of particles into plasma, which emit radiation as they are atomized. This radiation is received and transmitted by an optical fiber to be decomposed into different wavelengths and to generate a measurement of the spectrum. This technique is known as laser induced plasma spectroscopy and it analyzes the radiation emitted by particles that are atomized by a laser beam. The application of this technique requires the use of high-power laser devices capable of converting into plasma a portion of particles whose composition it is desired to be measured. The high-power laser systems impose high energy consumption, make the associated electronics more expensive, and require a careful handling to avoid accidents and deterioration of the other parts of the device to which they belong.

The same patent WO2006/138632 (A2), and the article 'Improved process control through real-time measurement of mineral content', of D. Turler, M. Karaca, W. B. Davis, R. Giauque and D. Hopkins, published on Nov. 2, 2001, available online at: 'http://www.osti.gov/bridge'; propose as an alternative to laser induced plasma spectroscopy to analyze the particle flow by means of fluorescence spectroscopy. In this type of spectroscopy the atoms of the illuminated particles absorb the received energy at a wavelength that allows them to re-emit the radiation in another wavelength; this phenomenon is known as fluorescence. This second wavelength depends on each atom and the analysis of the radiated wavelengths by fluorescence would allow identifying the constituents of the particle flow. The document 'Improved process control through real-time measurement of mineral content' proposes the use of X-ray radiation to induce the fluorescence phenomenon on the particles to be analyzed. In fluorescence spectroscopy short wavelengths are used, i.e., highly energy photons, to alter the energy levels of the electrons of the atoms that then will radiate due to fluorescence. The wavelengths of X-rays are in the range between 0.1 nm and 10 nm. X-rays require safe designs that make the implementation, certification, and use more expensive, because they are harmful to living tissue. Additionally, their high penetration level inside standard materials and their ionizing capacity forces complex electronic designs in the process of measuring the spectrum radiated by fluorescence.

Both the patent WO2006/138632 (A2) and the method proposed in the article 'Improved process control through real-time measurement of mineral content' assume taking a portion of the material excavated from the borehole, which may induce sampling errors when one considers that, for example, in the case of copper mining, smaller and more volatile particles, and therefore particles more likely to be lost, contain higher concentrations of valuable mineral.

The methods and devices described in the prior art involve a number of fixes and some inefficiencies, such as:

The exposure of the extracted dust and its handling alters its composition due to the loss of valuable particulate material. For example, smaller particles, and thus in general more volatile particles, are those that contain the highest grade in the copper mining industry; on the other hand, in deposits located in the desert the samples may be contaminated by dust that travels with the wind.

The choice of samples of different groups of debris taken from different pits introduces a bias in the ensemble of selected samples when it is not possible to analyze all the pits, a common situation in many types of analysis due to time requirements.

In the methods of laboratories, when samples are taken from the debris produced in the excavation of a pit and a value of grade is assigned to it, a bias is produced by not considering the distribution of the different presence of valuable minerals at different depths inside the same pit.

The analysis of laboratory samples usually restricts the amount of samples capable of being analyzed and delivers results after a certain time, during which it is not possible to take an informed decision about the mineral quality of the soil. This uncertainty is associated with a loss of time or a waste of resources when, as occurs in practice, it is decided to make rock blasting operations before the results of the analysis of grades are available.

The use of a high-energy laser beam for plasma induced emission spectroscopy imposes high energy consumption and designs that must consider the possible and undesired destructive effect of the laser beam on parts of the device that generates it; likewise, safety factors have to be considered in the design. The previously mentioned impositions make the design and the construction more expensive.

The fluorescence spectroscopy techniques require high-energy photon radiation of short wavelength. X-rays with photons that are more energetic than the ones of visible or infrared radiation facilitate the fluorescence but impose restrictions on the design due to their ability to ionize and their high degree of penetration into standard materials. These same characteristics make them harmful to living tissue. These characteristics imply high development, production, certification, and implementation costs. A similar thing happens with other wavelengths commonly used in fluorescence spectroscopy such as gamma rays and UV.

The drawbacks resulting from the application of traditional methods for the determination of the mineral quality of an exploitable soil imply losses due to the inefficient use of time and resources, and due to erroneous estimates produced by bias in the determination of a grade profile in depth and in distribution in the field that has been explored by means of drilling.

Technical Problem

In many production processes it is essential to know quickly and accurately the concentration of different compounds in products related to extraction processes of raw materials. In the particular case of mining it is necessary to know the concentration of valuable minerals in the portions of land that are susceptible to be processed to decide the commercial viability of extraction and to optimize the exploitation. There exists therefore the need to reduce the existing inefficiencies, the errors caused by taking biased samples, the inability to take in a reasonable time samples of all the pits at all depths and the alteration of the samples associated with the loss of valuable particulate material or the pollution with particles in suspension in the environment in the determination of the concentration of minerals of interest in the boreholes for the prospected soils.

Solution to the Problem

To solve the technical problems mentioned above, a technology has been designed that integrates the efficient collection and analysis of the dust produced in a perforation in the excavation site, in real time, in a non-intrusive and continuous manner.

The present invention consists in method and a system of collection and analysis for the in situ determination of concentrations of minerals in granular materials coming from a pit being excavated, on a continuous, non-intrusive, and real-time manner. According to the present invention, the collection of granular material passes towards a capturer of granulated material to be entered afterwards to a sensor module that determines the concentration of various minerals through spectroscopic methods. The collection of granular material stems from the perforation dust that goes up through the bit of a drill that is excavating. The information on the concentration of different minerals in the granular material that is being analyzed in that moment can be processed and transmitted to establish and/or correct logistical and operational procedures such as, e.g., in an excavation or for a global process in which it is set.

Advantageous Effects of Invention

The system and method of the present invention measures only the electromagnetic absorption of a dust mixture at certain wavelengths in the visible and infrared spectrum, to relate then these data with concentrations via calibrations that are performed by comparison with measurements produced by traditional methods. It is less cumbersome, less expensive, and above all faster to get the results than the methods, devices, and systems of the prior art. This speed and easiness, for example, allows, with the method and the system of the present invention, to decide whether to stop an excavation if one considers that the pit is sterile.

In addition to measuring the instantaneous concentration, one can record the depth of an excavation pit to be analyzed to associate a concentration at each depth. By means of this, the present invention can continuously analyze the dust excavated from a pit and generate a continuous profile of the concentration of a particular mineral as a function of pit depth.

This continuous mineral concentration profile is more accurate since it prevents the pollution and handling of the dust extracted from the pits; hence one obtains more accurate information associated exactly with the perforation site, saving time in the analysis and obtaining valuable information regarding the profile obtained in depth about the concentration of all types of ore; so that the important, costly, and irreversible decision making about rock blasting is more successful.

In the prior art an important part of the excavated material escapes the processes of analysis due to being more volatile. In the mining of copper, for example, where the percentage of copper in the soil is desired to be estimated, the particles that contain higher concentration of this mineral are the smaller ones and therefore the ones more likely to get lost in the handling or selection of a part of the dust cloud generated in the excavation of a pit. FIG. 1 displays the results of a study performed by Dr. Marcos Alfaro and displayed in the document 'Introduction to mine sampling', conducted for the Instituto de Ingenieros de Minas de Chile; Santiago, Chile, 2002. FIG. 1 shows the relationship between the size of the particles removed in the excavation of a pit and the copper content of them for a sample. The present invention includes a system and a method that avoids the loss of fine particles of the granular material so as to give more accurate values on mineral concentrations present in the pits being excavated.

DETAILED DESCRIPTION

Figure 1:
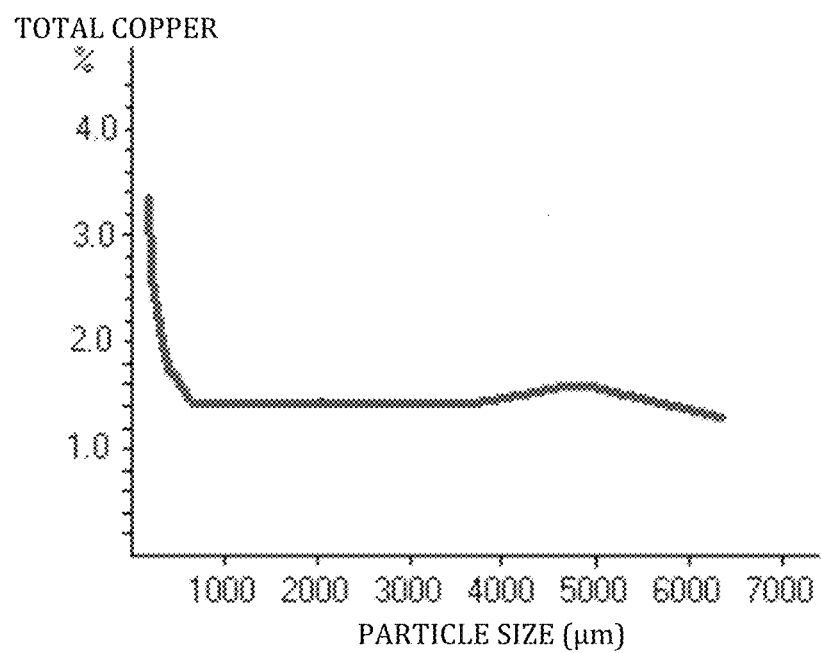
FIG. 1 shows the experimental results of measuring the amount of copper contained in particles of different sizes obtained from the excavation of a borehole.
Figure 2:
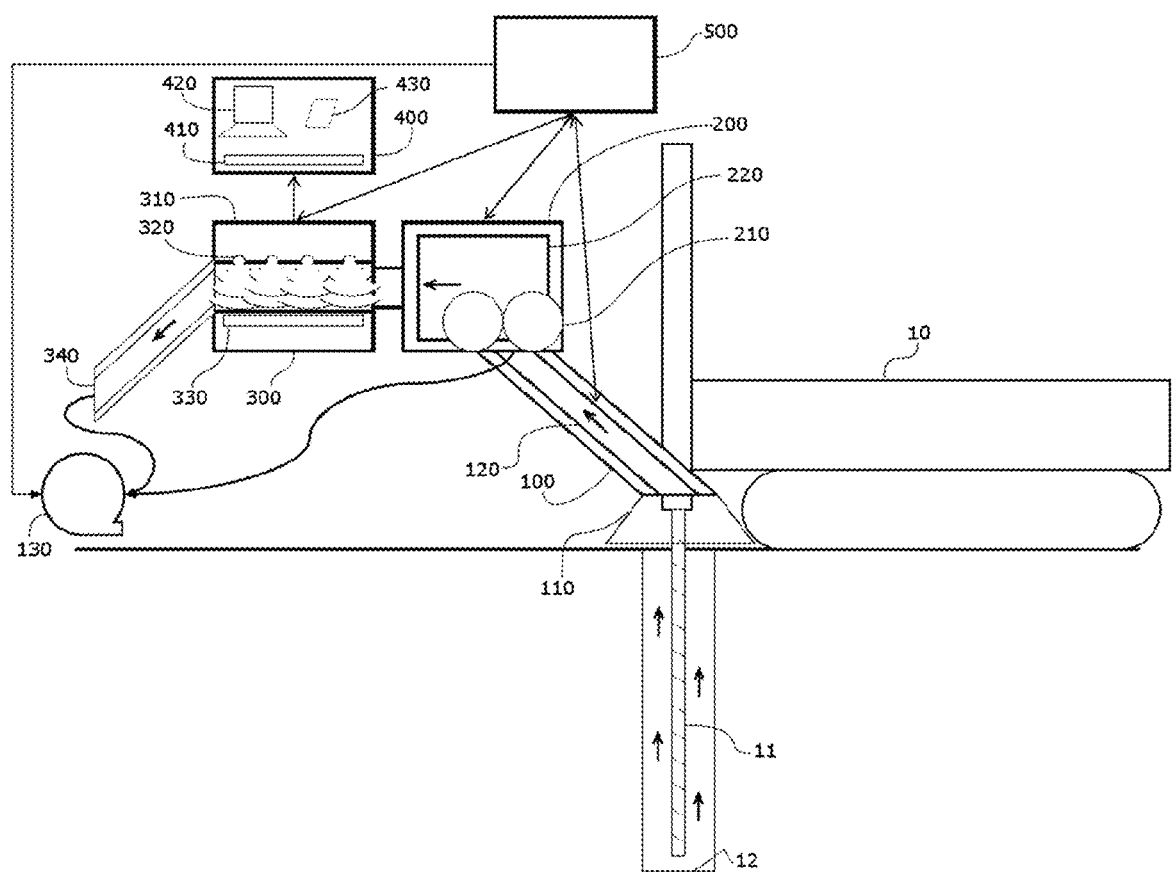
FIG. 2 illustrates schematically the system and method of the present invention.

According to this invention, the collection and analysis system for the in situ determination of mineral concentrations of granular material from a pit (12) being excavated, in a continuous, non-intrusive, and real-time manner, includes:

a collection module (100) of granulated material that comprises coupling means (110) for connecting operatively and capturing fine particulates, or dust, of the granular material to the auger (11) of a punch (10) excavating the pit (12), transportation media (120) of granular material that is connected to a conditioning module (200) of granular material through sieves to let particles smaller than 10 mm pass by, through this transport medium (120) an air flow circulates with speed between 1 m/s and 30 m/s generated by a vacuum pump, an air compressor or a blower (130) which allows the movement of the granulated material;

a conditioning module (200) of granular material comprising grinding media (210) to obtain a fine particulate matter with size less than 6 mm, the output of said grinding media is connected to a drying chamber (220) with drying means, said air flow moves the fine particulate material to said drying chamber (220) and said drying means comprise heating means for heating the air flow that carries the fine particulate material to a temperature lower than 100° C., said drying means include steam permeable means to remove the condensate from the heated air flow and leave the fine particulate material with a moisture content below 6%, said drying means comprise a cooling chamber where said flow of heated and dried air is cooled as it passes through heat exchangers to a temperature below 60° C.; said cooling chamber of the conditioning module is connected tightly to an absorption spectrum acquisition module (300);

an absorption spectrum acquisition module (300) connecting said cooling chamber of the conditioning module (300) in a sealed manner to a sensor chamber (310) through where said air flow circulates, which carries said fine particulate material, said sensor chamber (310) comprises a plurality of photo-emitters (320) as means of electromagnetic radiation with wavelengths between 0.2 and 20 microns, with a power of 0.1 mW to 800 W for each photo-emitter and sensing media (330) of this radiation arranged facing each other and on the opposite side of the photo-emitters (320) in said the sensor chamber (310) to obtain a spectroscopy of the fine particulate material flowing through the sensor chamber (310); said sensor chamber (310) connects to an outlet duct (340) that releases the particulate material out of the system;

an analysis and data transmission module (400) comprising analog-digital converters (410), computer media (420), and communication devices (430), wherein said analog to digital converters (410) are connected to the sensing devices (330) and convert the readings of the sensing devices (330) into digital values for their storage in said computer medium (420) and for their analysis by statistical comparison with samples of the calibration material; said communication devices (430) allow the transmission of the digital stored values and their analysis to a remote computational medium for the decision making respecting the mineral concentration of said granulated material.

According to yet another assembly of the present invention, a process of collection and analysis is provided for the in situ determination of mineral concentrations in granular material from a pit (12) being excavated, in a continuous, non-intrusive, and real-time manner, which comprises the steps of:

a) coupling means for coupling (110) to the auger (11) of a punch (10) excavating said pit to a collection module (100) to capture the entire granular material, including the finest dust;

b) collecting a stream of granular material through said coupling means (110) by a suction pump, air compressor, or blower (130) with an airflow between 1 m/s and 30 m/s, and sift the flow of granular material particle for a size less than 10 mm;

c) transporting said flow of granular material to a conditioning module (200) through a transport medium (120) such as a sleeve, a pipe, or a hose;

d) crushing said granulated material into a fine particulate matter with size less than 6 mm by grinding media (210) in the conditioning module (200), such as a jaw crusher, an impact crusher, a cone crusher, a vertical shaft crusher according to the origin of the granular material;

e) drying said fine particulate material in a drying chamber (220) heating said flow of fine particulate material to a temperature below 100° C., extracting the steam from said flow of fine particulate material to a moisture content below 6% and carry said flow of fine particulate material to a cooling chamber;

f) cooling said flow of fine particulate matter in the cooling chamber to a temperature below 60° C. with heat exchangers;

g) transporting said fine particulate matter flow by means of said airflow to a sensor chamber (310) in an absorption spectrum acquisition module (300);

h) irradiating said flow of fine particulate matter in said sensor chamber (310) with radiation of a wavelength between 0.2 to 20 microns by means of an array of photo-emitters (320), with a power between 0.1 mW to 800 W for each photo-emitter; and capture the emitted radiation that has passed through said flow of fine particulate matter by means of readings (330) such as an array of up to 70,000 discrete sensors such as avalanche photo-diodes and photo-transistors, or a charge-coupled device (CCD sensor) of up to 70,000 dots (pixels);

i) in an analysis and data transmission module (400), converting to digital values the reading captured from said array of photo-detectors by means of an analog-digital converter (410) for their storage on a computational medium (420), generating a value of instantaneous concentration of the present minerals, and simultaneously recording the depth of the boring machine (10) in the pit (12) that is being excavated from where the granular material stems generating a continuous spectroscopic profile of the granular material collected in function of to the recorded depth;

j) evacuating the flow of fine particulate material to an outlet duct (310) for their further storage, confinement, or later use in another application.

In addition, the method of the present invention comprises the stage of analyzing these digital values by using appropriate mathematical processes and statistical comparison with samples of calibration dust whose concentration of a compound of interest is previously known to obtain the mineral concentration of a valuable compound in the flow of fine particulate matter.

In addition, the method of the present invention comprises the stage of transmitting to a remote computer medium said digital values or the mineral concentration for decision making with respect to the mineral concentration of said granulated material.

MODE OF CARRYING OUT THE INVENTION

According to another aspect of the present invention, the collection and analysis system further comprises a control mechanism module (500) that performs the coordination and electronic control of said vacuum pump, air compressor, or blower (130), said grinding media (210), said drying chamber (220), said sensor chamber (310) with said photo-emitters (320) and said sensing means (330); which comprises a PXI or Compact RIO chassis with a protocol often used in industrial applications such as RS-485, Fieldbus, or Ethernet. This control mechanism module (500) performs control loops to control the flow of fine particulate material, preferably laminar, the temperature of said fine particulate material and the intensity of electromagnetic radiation used in the absorption spectrum acquisition module (300).

According to another assembly of the present invention, said coupling means (110) of the collection module (100) can be, e.g., a tight coupling, a clamp, a sleeve, or a duct opening in the form of a bell such as to capture all the dust, including the finer grained material. On the other hand, the transport media of the granular material may be for example a sleeve, a pipe, or a hose, preserving all the raised dust, including the finest dust of the granulated material. For example, in an analysis of mineral concentration of the granular material from an excavation pit (12), said sleeve reaches the pithead (12) and has a coupling to a portion of the auger (11) of a drilling machine (10) that protrudes from the shaft (12). According to another assembly of the present invention, a plurality of inlet ducts is located with their openings covering most of the pit's mouth without touching the auger (11) through which the air flow is inhaled or driven and the output of said ducts are connected to the conditioning module (200).

According to other assemblies of the invention, said grinding media (210) may include for example a jaw crusher, an impact crusher, a cone crusher, a vertical shaft crusher according to the origin of the granulated material, said drying media consist of a first duct in coil within a hot chamber, inside said air flow passes and is heated to 100° C., then said first duct in coil exits the hot chamber and enters into a condensing chamber with said vapor permeable media such as woven polypropylene membranes to extract the condensate of said air flow, then this condensation chamber connects with a cold chamber, inside said cold chamber the air flow circulates through heat exchangers to diminish the temperature of the airflow to less than 60° C., said heat exchangers may be of a plaque, or of a second duct in coil inside which said air flow circulates within said cooling chamber. Such heating means may consist in a convection for hot combustion gases, superheated steam, or radiation from an electrical resistance within said hot chamber. Such cooling means may be convection by forced air ventilation, liquid nitrogen, or circulating cold water.

Such sensing means (330) may include an array of photo-detectors such as up to 70,000 discrete sensors like avalanche photo-diodes and photo-transistors, or a charge-coupled device (CCD sensor) of up to 70,000 dots (pixels).

Said data transmission means (430) are for example a digital transmission network with fiber optics, coaxial cable, MODEM with phone cable or wireless, radio-frequency transmitters, satellite communications, etc.

Industrial Applicability

The invention has particular, but not exclusive, application in boreholes for the determination of grades in mining, geological exploration, perforations in concrete; especially useful in the mining industry and in the geological industry in general.

The invention claimed is:

1. Collection and analysis system for the in situ determination of mineral concentrations of granular material from a pit being excavated in a continuous, non-intrusive, and real-time manner, comprising:
   a collection module for collecting granular material comprising a coupling means operatively connected to an auger of a drilling machine excavating said pit;
   transportation media for the granular material;
   a conditioning module connected to the transportation media wherein the conditioning module comprises sieves to pass particles of the granular material smaller than 10 mm;
   a vacuum pump generating air flow through said transportation media;
   an air compressor or a fan that allows the transport of the granular material;
   a conditioning module comprising grinding media;
   a drying chamber connected to the output of the grinding media, the drying chamber comprising a drying means, said drying means comprising a heating means for heating the air flow that carries the granular material;
   a vapor permeable media to extract condensate from the flow of heated air;
   a cooling chamber with heat exchangers where the flow of heated air is cooled and dried wherein said cooling chamber of the conditioning module connects tightly to an absorption spectrum acquisition module;
   said absorption spectrum acquisition module connects said cooling chamber of the conditioning module tightly to a sensor chamber where the circulating air flow carries the granular material, wherein said sensor chamber includes a plurality of photo-emitters emitting electromagnetic radiation and a sensing means disposed on a side of the sensor chamber opposite to the plurality of photo-emitters, wherein the sensor chamber is connected to an outlet duct releasing fine particulate matter out of the system; and
   an analysis and data transmission module comprising analog-digital converters, computer media and digital media, wherein said analog to digital converters are connected to the sensing means.

2. The system of claim 1, wherein said air flow has a speed of 1 m/s and 30 m/s.

3. The system of claim 1, wherein said grinding media may include a jaw crusher, an impact crusher, a cone crusher or a vertical shaft crusher.

4. The system of claim 1, wherein said drying means is a first duct in coil within a hot chamber, wherein the air flow passes through said hot chamber, and enters a condensing chamber connected to said cooling chamber, wherein said condensing changer comprises said vapor permeable media to extract condensate from the flow of heated air.

5. The system of claim 4, wherein said heating means consists of convection hot combustion gases, superheated steam, or radiation from an electrical resistance within said hot chamber.

6. The system of claim 1, wherein said vapor permeable media comprises woven polypropylene membranes.

7. The system of claim 1, wherein said heat exchangers comprise a motherboard, or a second product in coil inside the air flow circulating within said cooling chamber.

8. The system of claim 1, wherein said cooling chamber includes cooling means comprising convection forced air ventilation, liquid nitrogen or cold water circulation.

9. The system of claim 1, wherein said plurality of photo-emitters emit a wavelength between 0.2 and 20 microns and operate within a power range of between 0.1 mW to 800W per photo-emitter.

10. The system of claim 1, further comprising a control module that electronically controls the vacuum pump, said air compressor or the fan, said grinding media, said drying means, and said plurality of photo-emitters.

11. The system of claim 1, wherein said coupling means is a tight coupling or bell-shaped vent opening and the transportation media comprises a sleeve, a pipeline or a hose.

12. The system of claim 1, wherein said sensing means consists of an array of photo detectors comprising up to 70,000 discrete sensors.

13. A process of collection and analysis for the in situ determination of concentrations of granular material from a well being dug comprising the steps of:
    capturing the granular material and coupling it to the auger of a drill digging the well using a coupling means;
    collecting a stream of the granular material through said coupling means by a suction pump, air compressor or fan with airflow of 1 m/s and 30 m/s and using a sieve to pass the granular material flow smaller than 10 mm;
    transporting the flow of granular material to a conditioning module;
    crushing said granular material into a fine particulate matter with a size less than 6mm by means of grinding in in a conditioning module;
    drying said fine particulate matter in a drying chamber, heating a flow of the particulate matter to a temperature below 1000 degrees Celsius lowering the moisture content of said flow of the particulate matter to a moisture content below 6% and transporting the flow of fine particulate material to a cooling chamber,
    cooling said flow of particulate matter by cooling the cooling chamber to a temperature below 60° C. with a heat exchanger;
    transporting said flow of particulate matter through said air flow to a reading chamber;
    irradiating the flow of particulate matter in the reading chamber with radiation having a wavelength between 0.2 to 20 microns with an array of photo-emitters;
    capturing the radiation that has passed through the flow of fine particulate material without being absorbed by an array of photo detectors;
    converting the captured radiation into a digital reading for storage in a computational analysis module;
    generating an instantaneous value of concentration of minerals present, and simultaneously recording the depth of the drill in the excavation pit from which the granular material was collected;
    generating a continuous spectroscopic profile of the granular material collected according to the depth recorded; and
    evacuating the flow of fine particulate matter to an outlet duct for further storage, confinement, or later use in another application.

14. The process according to claim 13, further comprising the steps of remotely transmitting digital values representing at least one of the instantaneous value of mineral concentrations and the continuous spectroscopic profile.

15. The process according to claim 13, wherein said coupling means is a tight coupling or bell-shaped vent opening.

16. The process according to claim 13, wherein transporting the flow of granular material is facilitated by at least one of a sleeve, pipeline, or hose.

* * * * *